United States Patent [19]

Ansmann

[11] Patent Number: 4,798,682

[45] Date of Patent: Jan. 17, 1989

[54] OIL-IN-WATER EMULSIONS WITH INCREASED VISCOSITY UNDER SHEAR STRESS

[75] Inventor: Achim Ansmann, Hilden, Fed. Rep. of Germany

[73] Assignee: Henkel Kommanditgesellschaft auf Aktien, Duesseldorf, Fed. Rep. of Germany

[21] Appl. No.: 872,306

[22] Filed: Jun. 6, 1986

[30] Foreign Application Priority Data

Jun. 18, 1985 [DE] Fed. Rep. of Germany ....... 3521713

[51] Int. Cl.$^4$ .......................... B01J 13/00; C08L 1/26; A61K 7/06

[52] U.S. Cl. .................................. 252/312; 524/832; 424/70; 514/844

[58] Field of Search ....................... 252/312; 524/832; 106/197.1; 424/70; 514/844

[56] References Cited

U.S. PATENT DOCUMENTS

| | | | |
|---|---|---|---|
| 2,550,211 | 4/1951 | Watters | 252/312 |
| 2,798,053 | 7/1957 | Brown | 260/2.2 |
| 3,047,353 | 7/1962 | Klein | 252/312 |
| 3,527,712 | 9/1970 | Renn et al. | 252/312 |
| 3,615,497 | 10/1971 | Fassbender et al. | 252/312 |
| 3,666,690 | 5/1972 | Bann | 252/312 |
| 4,253,999 | 3/1981 | Okishi | 252/312 |
| 4,547,308 | 10/1985 | Torerbeck | 252/312 |
| 4,576,645 | 3/1986 | Ravel et al. | 252/312 |

OTHER PUBLICATIONS

Brookfield Engineering Laboratories, Inc., pp. 1, 3, 10–11.

*Primary Examiner*—Matthew A. Thexton
*Assistant Examiner*—Catherine S. Kilby
*Attorney, Agent, or Firm*—Ernest G. Szoke; Wayne C. Jaeschke; Mark A. Greenfield

[57] ABSTRACT

Oil-in-water emulsions show improved viscosity behavior, more especially an increased viscosity under shear stress, when the continuous aqueous phase contains a combinations of hydrocolloids comprising: (a) at least one water-soluble nonionic cellulose ether; and (b) a cross-linked acrylic acid polymer or copolymer having a weight average molecular weight of from 1,000,000 to 5,000,000; in the form of a water-soluble salt in a quantitative ratio a:b of from 9:1 to 1:9. Cosmetic O/W-creams according to the invention show more "body" when applied to and spread over the skin.

20 Claims, No Drawings

OIL-IN-WATER EMULSIONS WITH INCREASED VISCOSITY UNDER SHEAR STRESS

BACKGROUND OF THE INVENTION

1. Field of the Invention

This invention relates to oil-in-water emulsions (hereinafter referred to as O/W-emulsions) and, more particularly, to topical, cosmetic and pharmaceutical preparations in the form of an O/W-emulsion.

2. Statement of Related Art

The viscosity and rheological behavior of O/W-emulsions are determined on the one hand by the nature, quantity and fineness of the disperse phase and, on the other hand, by the composition of the continuous aqueous phase. In the case of emulsions intended for the care of hard surfaces or for dermatocosmetic, trichocosmetic, or pharmaceutical topical applications, rheological behavior has a considerable bearing on the subjective feeling on application.

Emulsions for cosmetic application to the skin are expected by the user to create a nourishing feeling when rubbed onto the skin. However, any increase in the proportion of oil phase often leads to an undesirable greasy feeling on the skin.

For this reason, water-soluble polymers, specifically hydrocolloids, have been added to the aqueous phase in order to control its viscosity. In the case of cosmetic and pharmaceutical topical O/W-emulsions, it is known to use water-soluble vegetable gums, such as alginates and tragacanth, water-soluble cellulose derivatives, such as carboxymethyl cellulose, hydroxyethyl cellulose, methyl cellulose, water-soluble starch derivatives and synthetic polymers, such as polyvinylalcohol, polyethylene oxides or polyacrylic acids, in order to thicken the aqueous phase and to stabilize the emulsions.

Aqueous solutions of these polymers, like solutions of most water-soluble polymers, show structural viscosity, in other words their viscosity decreases under the effect of shear forces. O/W-emulsions of which the aqueous phase is thickened by structurally viscous polymers such as these are attended by the disadvantage that, when the emulsion is rubbed onto the skin, there is little of the viscosity to be felt on account of the shear forces generated during rubbing, so that the emulsions lack substance and have little cosmetic appeal.

DESCRIPTION OF THE INVENTION

The present invention provides less shear-dependent thickeners for the aqueous phase of O/W-emulsions and provides O/W-emulsions which, without additionally increasing the oil phase, have more "body," i.e. improved viscosity behavior and cosmetically more satisfactory behavior when applied to and rubbed into the skin or hair.

The present invention affords oil-in-water emulsions having a discontinuous oil phase and a continuous, aqueous phase, characterized in that the continuous aqueous phase contains a combination of hydrocolloids comprising: (a) at least one water-soluble nonionic cellulose ether; and (b) at least one cross-linked acrylic acid polymer or copolymer water-soluble salt having a weight average molecular weight of from 1,000,000 to 5,000,000; in a quantitative ratio a:b of from 9:1 to 1:9 preferably 1:3 to 3:1, most preferably 1:1. The invention is based on the observation that aqueous solutions of these hydrocolloids in combination with one another show an increased viscosity, particularly under the effect of shear forces, which is synergistically increased in comparison to the viscosities of solutions of the individual components.

Suitable water-soluble nonionic cellulose ethers are, preferably, methyl cellulose, hydroxyethyl cellulose, hydroxypropyl cellulose and/or methylhydroxypropyl cellulose. Hydroxypropyl cellulose and methylhydroxypropyl cellulose are particularly preferred. Hydroxypropyl celluloses are commercially available inter alia under the trademark "KLUCEL" (Hercules), while methylhydroxypropyl celluloses are commercially available inter alia under the trademark "VISCONTRAN" MHPC (Henkel KGaA).

The various commercial types of nonionic cellulose ethers of the type in question differ from one another in the degree of substitution and in the degree of degradation of the cellulose (i.e. the weight average molecular weight), giving qualities of varying solution viscosity.

Suitable methylhydroxypropyl cellulose has a viscosity, when in the form of 2% by weight aqueous solution, of from 40 to 40,000 mPas at 20° C. (as measured with a Brookfield rotational viscosimeter at 30 r.p.m.).

Suitable crosslinked acrylic acid polymers are products obtained by copolymerization of acrylic acid with from 0.1 to 4.0% by weight of a polyalkenyl polyether of a polyhydric alcohol containing more than one alkenylether moiety in the molecule as a crosslinking agent. One example of such a crosslinking agent is a polyallyl sucrose.

Other comonomers may optionally be used in the production of the crosslinked acrylic acid polymers in quantities of up to 59% by weight, based on the monomer mixture. Suitable comonomers include maleic acid anhydride, N-methylacrylamide, methylvinylether or mixtures of these additional monomers. Acrylic acid polymers of the type in question are known from U.S. Pat. No. 2,798,053, the disclosure of which is incorporated herein by reference, and are commercially available under the trademark "CARBOPOL" from B. F. Goodrich Chemical Company, U.S.A. The crosslinked acrylic acid polymers may be dispersed in water, although the desired strong thickening effect is only achieved when the polymers are converted into the salt form by inorganic bases, such as sodium hydroxide, potassium hydroxide, ammonia, or by low molecular weight amines or alkanolamines.

Suitable acrylic acid polymers have a viscosity of from 1,000 to 100,000 mPas when in the form of a 1% by weight aqueous solution neutralized with sodium hydroxide (as measured with a Brookfield rotational viscosimeter at 20 r.p.m., 20° C. and pH 7–8).

Oil-in-water emulsions according to the invention contain a discontinuous (inner) oil phase which comprises, and preferably consists essentially of cosmetic or pharmaceutical oil components, fats and/or waxes, oil-soluble emulsifiers and, optionally, oil-soluble pharmaceutical or cosmetic agents.

Suitable cosmetic oil components are any of the known vegetable, animal, mineral and synthetic oils, such as olive oil, sunflower oil, corn oil, mink oil, paraffin oil, silicone oils (for example dimethylpolysiloxane), squalene, olyelalcohol, 2-octyldodecanol, decyloleate, isopropylmyristate, isononlystearate, 2-ethylhexylpalmitate, glycerol tricaprylate and other esters, alcohols or hydrocarbons known as cosmetic oil components. Suitable cosmetic fats and waxes are any of the known products with melting points of up to about 80° C., such as hardened vegetable and animal fats (triglycerides); fatty alcohols, such as cetyl alcohol and stearyl alcohol; esters such as cetylpalmitate; natural waxes such as wool wax, beeswax, japan wax, carnauba wax, and candelilla wax; mineral waxes such as montan wax, paraffins, and vaseline; and synthetic paraffins such as the polyethylene waxes.

Suitable oil-soluble emulsifiers are any of those which are capable of emulsifying the above mentioned oils, fats and waxes. Examples of oil-soluble emulsifiers such as these are: the soaps of $C_{12-22}$ fatty acids; the monoglycerides and diglycerides and the sorbitan partial esters of $C_{12-22}$ fatty acids, and the adducts of from 2 to 30 mols of ethylene oxide with such fatty acid partial glycerides and sorbitan fatty acid esters; the adducts of from 2 to 30 mols of ethylene oxide with $C_{12-22}$ fatty alcohols, with $C_{12-22}$ fatty acids, with alkylphenols containing from 8 to 16 carbon atoms in the alkyl group and with fatty acid alkanolamides; $C_{16-22}$ fatty alcohol sulfates in the form of their alkali or alkanolammonium salts; and/or phosphoric acid esters of linear fatty alcohols or of fatty alcohol polyglycol ethers in the form of their alkali or alkanolammonium salts.

In addition to the constituents mentioned above, the discontinuous oil phase may also contain oil-soluble agents such as light stabilizers, antioxidants, vitamins, oil-soluble preservatives (for example p-hydroxybenzoic acid benzylester), and/or pharmaceutical agents.

In addition to the combination of hydrocolloids present in accordance with the invention, the continuous aqueous phase may also contain other water-soluble auxiliaries such as: polyols, for example glycerol or sorbitol; water-soluble salts, for example magnesium sulfate; buffers, for example alkali phosphate, alkali citrate and/or borates; water-soluble preservatives, for example p-hydroxybenzoic acid methylester, sorbic acid; water-soluble surfactants or emulsifiers; water-soluble dyes or water-soluble cosmetic or pharmaceutical agents, for example water-soluble vegatable extracts, water-soluble proteins or protein derivatives, aminoacids; and the like, or their mixtures.

The O/W-emulsions according to the invention contain the oil phase and the aqueous phase preferably in a ratio by weight of from 1:9 to 4:6, that is, the oil phase constitutes 10% to 40% of the total emulsion. The combination of hydrocolloids used in accordance with the invention should be present in a quantity of from about 0.2 to 2.0%, preferably 0.3 to 1.0% by weight, based on the weight of the emulsion as a whole.

The O/W-emulsions according to the invention may be of liquid or creamy consistency. In either case, the O/W-emulsions according to the invention show better viscosity behavior than known compositions and, when applied to and rubbed into the skin, create a cosmetically better, richer impression than corresponding emulsions containing only one of the two hydrocolloid components alone. The invention is further illustrated by the following Examples:

EXAMPLES

1. Viscosity behavior of aqueous solutions of hydrocolloids

The viscosity of the following aqueous solutions was measured at various shear velocities:

(a)
  0.5% by weight "Viscontran" MHPC 3000[8]
  99.5% by weight water (b)
  0.5% by weight "Carbopol" 940[10]
  99.5% by weight water, triethanolamine to pH=7

(c)
  0.5% by weight "Viscontran" MHPC 3000[8]
  0.5% by weight "Carbopol" 940[10]
  99.0% by weight of water, triethanolamine to pH=7

The viscosity measurements were carried out with a Haake Rotovisko rotational viscosimeter at 20° C. The following viscosities were calculated from the shear strengths measured at the various shear velocities:

| Shear velocity ($s^{-1}$) | Viscosity of the solution (mPas) | | |
| --- | --- | --- | --- |
| | a | b | c |
| 10 | 140 | 18,000 | 25,400 |
| 28 | 135 | 9,200 | 14,000 |
| 56 | 130 | 5,400 | 8,500 |
| 112 | 120 | 3,100 | 5,000 |

It can be seen that solution c has a synergistically increased viscosity over the entire shear range, particularly at low shear velocities, in that the result of combining the two hydrocolloids is much greater than the result of either of them taken alone.

2. Invention Examples (ingredients)

2.1 Night cream, O/W

| | % by weight |
| --- | --- |
| "Cutina" MD[1] | 2.0 |
| Cetyl alcohol | 2.0 |
| "Eumulgin" B1[2] | 1.0 |
| "Eumulgin" B2[3] | 1.0 |
| 2-octyldodecanol | 8.0 |
| "Myritol" 318[5] | 3.0 |
| Paraffin oil, thin-flowing | 3.0 |
| "Hydagen" F[6] | 0.2 |
| "Viscontran" MHPC 6000[7] | 0.2 |
| "Carbopol" 940[10] | 0.4 |
| Triethanolamine | 0.8 |
| Water q.s. to | 100.0 |

2.2 Moisturizing cream, O/W

| | % by weight |
| --- | --- |
| Cetyl/stearyl alcohol (50:50) | 8.0 |
| Palmitic/stearyl acid (50:50) | 4.0 |
| "Eumulgin" B3[4] | 1.5 |
| Paraffin oil, thick-flowing | 4.0 |
| 2-octyldodecanol | 8.0 |
| "Hydagen" F[6] | 1.0 |
| Triethanolamine | 1.8 |
| "Carbopol" 940[10] | 0.5 |
| "Viscontran" MHPC 3000[8] | 0.5 |
| Water q.s. to | 100.0 |

2.3 Skin-care cream, O/W

| | % by weight |
| --- | --- |
| "Cutina" KD16[13] | 5.0 |
| 2-octyldodecanol | 4.0 |
| Paraffin oil, thin-flowing | 4.0 |
| Cetyl alcohol | 2.0 |
| Glycerol, 86% by weight | 3.0 |
| Potassium hydroxide | 0.25 |
| "Carbopol" 934[11] | 0.2 |
| "Viscontran" MHPC 6000[7] | 0.3 |
| Water q.s. to | 100.0 |

2.4 Body lotion, O/W

|  | % by weight |
| --- | --- |
| "Cutina" MD(1) | 4.0 |
| Palmitic/stearic acid (50:50) | 4.0 |
| Cetyl/stearyl alcohol | 2.0 |
| "Eumulgin" B2(3) | 2.0 |
| 2-octyldodecanol | 3.0 |
| "Myritol" 318(5) | 3.0 |
| "Carbopol" 940(10) | 0.2 |
| "Viscontran" MHPC 3000(8) | 0.6 |
| Triethanolamine | 1.5 |
| Water q.s. to | 100.0 |

2.5 Cleansing emulsion, O/W

|  | % by weight |
| --- | --- |
| "Cutina" MD(1) | 5.0 |
| Palmitic/stearic acid (50:50) | 5.0 |
| Cetyl/stearyl alcohol | 2.0 |
| "Eumulgin" B1(2) | 1.0 |
| "Eumulgin" B2(3) | 1.0 |
| 2-octyldodecanol | 10.0 |
| "Myritol" 318(5) | 5.0 |
| "Carbopol" 940(10) | 0.4 |
| "Viscontran" MHPC 6000(7) | 0.2 |
| Triethanolamine | 1.5 |
| Water q.s. to | 100.0 |

2.6 Moisturizing emulsion, O/W

|  | % by weight |
| --- | --- |
| Palmitic/stearic acid (50:50) | 4.0 |
| Cetyl/stearyl alcohol | 2.0 |
| "Eumulgin" B2(3) | 2.0 |
| Isopropylmyristate | 5.0 |
| 2-octyldodecanol | 2.0 |
| "Myritol" 318(5) | 3.0 |
| "Hydagen" F(6) | 3.0 |
| "Carbopol" 941(12) | 0.7 |
| "Viscontran" MHPC 3000(8) | 0.6 |
| Triethanolamine | 1.5 |
| Water q.s. to | 100.0 |

2.7 Skin-care milk, O/W

|  | % by weight |
| --- | --- |
| Paraffin oil, thin-flowing | 4.0 |
| "Hostaphat" KW 340 N(9) | 4.0 |
| 2-octyldodecanol | 8.0 |
| Cetyl/stearyl alcohol | 1.0 |
| "Eumulgin" B1(2) | 1.0 |
| Glycerol, 99.5% | 1.0 |
| Triethanolamine | 0.15 |
| Vegetable extracts, aqueous | 10.0 |
| "Carbopol" 940(10) | 0.2 |
| "Viscontran" MHPC 3000(8) | 0.3 |
| Water q.s. to | 100.0 |

The following trademarks were used in formulations 2.1 to 2.7.

(1) "Cutina" MD: a mixture of mono- and diglycerides of palmitic and stearic acids (Henkel KgaA;, Duesseldorf, F.R. Germany; Henkel Corp. Ambler, PA, U.S.A.)

(2) "Eumulgin" B1: cetyl/stearyl alcohol+12 mols ethylene oxide (Henkel KGaA, Henkel Corp.)

(3) "Eumulgin" B2: cetyl/stearyl alcohol+20 mols ethylene oxide (Henkel KGaA, Henkel Corp.)

(4) "Eumulgin" B3: cetyl/stearyl alcohol+30 mols ethylene oxide (Henkel KGaA, Henkel Corp.)

(5) "Myritol" 318: caprylic-capric acid triglyceride (Henkel KGaA, Henkel Corp.)

(6) "Hydagen" F: Sodium salt of a polyhydroxy carboxylic acid (Henkel KGaA, Henkel Corp.)

(7) "Viscontran" MHPC 6000: methylhydroxypropylcellulose, viscosity 2% in distilled water (20° C., Brookfield viscosimeter, 20 r.p.m.) 5200–6500 mPas (Henkel KGaA, Henkel Corp.)

(8) "Viscontran" MHPC 3000: methylhydroxypropylcellulose, viscosity 2% in distilled water (20° C., Brookfield viscosimeter, 20 r.p.m.) 2900–4400 mPas (Henkel KGaA, Henkel Corp.)

(9) "Hostaphat": phosphoric acid ester of a wax alcohol+4 mols ethylene oxide adduct (Hoechst AG; F.R. Germany)

(10) "Carbopol" 940: a crosslinked acrylic acid polymer, weight average molecular weight approx. 4,000,000 (B. F. Goodrich Chem. Co., Avon Lake, Ohio, U.S.A.)

(11) "Carbopol" 934: a crosslinked acrylic acid polymer, weight average molecular weight approx. 3,000,000 (B. F. Goodrich Chem. Co.)

(12) "Carbopol" 941: a crosslinked acrylic acid polymer, weight average molecular weight approx. 1,250,000 (B. F. Goodrich Chem. Co.)

(13) "Cutina" KD 16: a mixture of mono and diglycerides of higher saturated fatty acids with potassium stearate (Henkel KGaA, Henkel Corp.).

I claim:

1. An oil-in-water emulsion having increased viscosity under shear stress comprising a continuous aqueous phase and a discontinuous oil phase, wherein said continuous aqueous phase contains a combination of hydrocolloids consisting essentially of:
   (a) at least one water-soluble nonionic cellulose ether; and
   (b) at least on water-soluble salt of a crosslinked acrylic acid polymer or acrylic acid copolymer having a weight average molecular weight of about 1,000,000 to 5,000,000,
   in a ratio a:b by weight of about 9:1 to about 1:9.

2. The emulsion of claim 1 wherein:
   (a) has a viscosity, when in the form of a 2% by weight aqueous solution, of from about 40 to about 40,000 mPas at 20° C., as measured on a Brookfield rotational viscometer at 30 r.p.m.

3. The emulsion of claim 1 wherein:
   (a) is at least one methyl cellulose, hydroxyethyl cellulose, hydroxypropyl cellulose, or methylhydroxypropyl cellulose.

4. The emulsion of claim 1 wherein:
   (a) is at least one hydroxypropyl cellulose, or methylhydroxypropyl cellulose.

5. The emulsion of claim 1 wherein:
   (b) is at least one copolymerization reaction product of acrylic acid with about 0.1 to about 4.0% by weight based on the copolymer weight of a polyalkenyl polyether of a polyhydric alcohol containing more than one alkenylether moiety in the molecule as a crosslinking agent.

6. The emulsion of claim 5 wherein said crosslinking agent is a polyallyl sucrose.

7. The emulsion of claim 1 wherein:
   (b) is a salt of: sodium hydroxide, potassium hydroxide, ammonia, a low molecular weight amine or a low molecular weight alkanolamine.

8. The emulsion of claim 5 wherein:

(b) is a salt of: sodium hydroxide, potassium hydroxide, ammonia, a low molecular weight amine or a low molecular weight alkanolamine.

9. The emulsion of claim 2 wherein:
(b) is at least one copolymerization reaction product of acrylic acid with about 0.1 to about 4.0% by weight based on the copolymer weight of a polyalkenyl polyether of a polyhydric alcohol containing more than one alkenylether moiety in the molecule as a crosslinking agent.

10. The emulsion of claim 3 wherein:
(b) is at least one copolymerization reaction product of acrylic acid with about 0.1 to about 4.0% by weight based on the copolymer weight of a polyalkenyl polyether of a polyhydric alcohol containing more than one alkenylether moiety in the molecule as a crosslinking agent.

11. The emulsion of claim 4 wherein:
(b) is at least one copolymerization reaction product of acrylic acid with about 0.1 to about 4.0% by weight based on the copolymer weight of a polyalkenyl polyether of a polyhydric alcohol containing more than one alkenylether moiety in the molecule as a crosslinking agent.

12. The emulsion of claim 1 wherein the ratio a:b is about 1:3 to 3:1.

13. The emulsion of claim 1 wherein the ratio a:b is about 1:1.

14. The emulsion of claim 11 wherein the ratio a:b is about 1:3 to 3:1.

15. The emulsion of claim 1 wherein said combinatin of hydrocolloids is present in a total amount of about 0.2 to about 2% by weight, based upon the total weight of the emulsion.

16. The emulsion of claim 14 wherein said combination of hydrocolloids is present in a total amount of about 0.2 to about 2% by weight, based upon the total weight of the emulsion.

17. The emulsion of claim 1 wherein said combination of hydrocolloids is present in a total amount of about 0.3 to about 1% by weight, based upon the total weight of the emulsion.

18. The emulsion of claim 14 wherein said combination of hydrocolloids is present in a total amount of about 0.3 to about 1% by weight, based upon the total weight of the emulsion.

19. The emulsion of claim 1 wherein said discontinuous oil phase and said continuous aqueous phase are present in a weight ratio of about 1:9 to about 4:6.

20. The emulsion of claim 18 wherein said discontinuous oil phase and said continuous aqueous phase are present in a weight ratio of about 1:9 to about 4:6.

* * * * *